(12) United States Patent
Liou

(10) Patent No.: US 11,678,839 B2
(45) Date of Patent: Jun. 20, 2023

(54) DEVICE FOR PERFORMING ANGIOGRAPHY AND PHOTOTHERAPY

(71) Applicant: Taipei Medical University, Taipei (TW)

(72) Inventor: Jian-Chiun Liou, Hsinchu (TW)

(73) Assignee: Taipei Medical University, Taipei (TW)

( * ) Notice: Subject to any disclaimer, the term of this patent is extended or adjusted under 35 U.S.C. 154(b) by 163 days.

(21) Appl. No.: 17/231,749

(22) Filed: Apr. 15, 2021

(65) Prior Publication Data
US 2022/0192594 A1  Jun. 23, 2022

(30) Foreign Application Priority Data

Dec. 23, 2020 (TW) ................. 109145790

(51) Int. Cl.
*A61B 5/00* (2006.01)
*A61B 5/02* (2006.01)
*A61B 5/1455* (2006.01)
*A61N 5/06* (2006.01)

(52) U.S. Cl.
CPC .......... *A61B 5/4836* (2013.01); *A61B 5/0013* (2013.01); *A61B 5/02007* (2013.01); *A61B 5/14552* (2013.01); *A61N 5/06* (2013.01); *A61B 2562/0238* (2013.01); *A61B 2562/04* (2013.01); *A61N 2005/0626* (2013.01); *A61N 2005/0652* (2013.01); *A61N 2005/0659* (2013.01)

(58) Field of Classification Search
CPC . A61B 5/4836; A61B 5/0013; A61B 5/02007; A61B 5/14552; A61B 2562/0238; A61B 2562/04; A61B 5/02416; A61B 5/6826; A61B 5/0059; A61B 5/14551; A61B 5/681; A61N 5/06; A61N 2005/0626; A61N 2005/0652; A61N 2005/0659; A61N 2005/0602; A61N 5/0613; A61N 2005/0629; A61N 2005/0645; A61N 2005/0651; A61N 2005/0667
See application file for complete search history.

(56) References Cited

U.S. PATENT DOCUMENTS

2019/0373687 A1* 12/2019 Williams ............... H05B 45/46
2020/0281512 A1*  9/2020 Grubb .................... A61B 5/489

* cited by examiner

*Primary Examiner* — Brian T Gedeon
*Assistant Examiner* — Joshua Andrew Schum-Houck
(74) *Attorney, Agent, or Firm* — Blank Rome LLP

(57) ABSTRACT

A device includes an angiography module, a phototherapy module, a carrier including an optical filter and accommodating the angiography module and the phototherapy module, and a control unit controlling operation of the angiography module and the phototherapy module. The angiography module includes infrared LEDs emitting infrared light through the optical filter to irradiate a limb of a subject, and an infrared sensor sensing a part of the infrared light reflected off the limb to generate a result, based on which the control unit generates an angiogram. The phototherapy module emits infrared light through the optical filter to irradiate the limb for phototherapy.

12 Claims, 7 Drawing Sheets

DEVICE FOR PERFORMING ANGIOGRAPHY AND PHOTOTHERAPY

CROSS-REFERENCE TO RELATED APPLICATION

This application claims priority of Taiwanese Invention Patent Application No. 109145790, filed on Dec. 23, 2020.

FIELD

The disclosure relates to a medical device, and more particularly to a device for performing angiography and phototherapy on a subject.

BACKGROUND

An arteriovenous (AV) fistula or an AV graft, which is a passageway between an artery and a vein, provides a vascular access for hemodialysis treatments. Phototherapy with infrared light can help integration of the AV fistula (or the AV graft) with blood vessel (s) of the patient, and prevent necrosis. In addition, phototherapy with infrared light promotes blood circulation, increases amount of blood flowing in the AV fistula (or the AV graft), and prevents thrombus and bacterial infection. Thus, a service life of the AV fistula (or the AV graft) may be extended. However, it is difficult to detect or assess damages to the AV fistula (or the AV graft), which may be caused by needle-punctures in hemodialysis treatments, and thus it is difficult to appropriately restore functionality of the AV fistula (or the AV graft) in time.

SUMMARY

Therefore, an object of the disclosure is to provide a device that is for performing angiography and phototherapy on a subject and that can alleviate at least one of the drawbacks of the prior art.

According to the disclosure, the device includes a carrier, an angiography module, a phototherapy module and a control unit.

The carrier is configured to be disposed on a limb of the subject. The carrier includes a housing that is configured to abut against the limb, that defines an accommodating space having an opening to face the limb, and that includes an optical filter closing the opening of the accommodating space.

The angiography module is disposed in the accommodating space of the housing. The angiography module includes a plurality of first infrared light-emitting diodes (LEDs) and an infrared sensor. The plurality of first infrared LEDs are configured to emit first infrared light through the optical filter to irradiate the limb. The infrared sensor is configured to sense a part of the first infrared light reflected off the limb to generate a result of sensing.

The phototherapy module is disposed in the accommodating space of the housing. The phototherapy module includes a plurality of second infrared LEDs. The plurality of second infrared LEDs are configured to emit second infrared light through the optical filter to irradiate the limb for phototherapy.

The control unit is coupled to the angiography module and the phototherapy module to communicate therewith. The control unit includes an optical-component control module and an image processing module. The optical-component control module is configured to control operation of the angiography module and the phototherapy module. The image processing module is configured to generate an angiogram based on the result of sensing generated by the infrared sensor of the angiography module.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
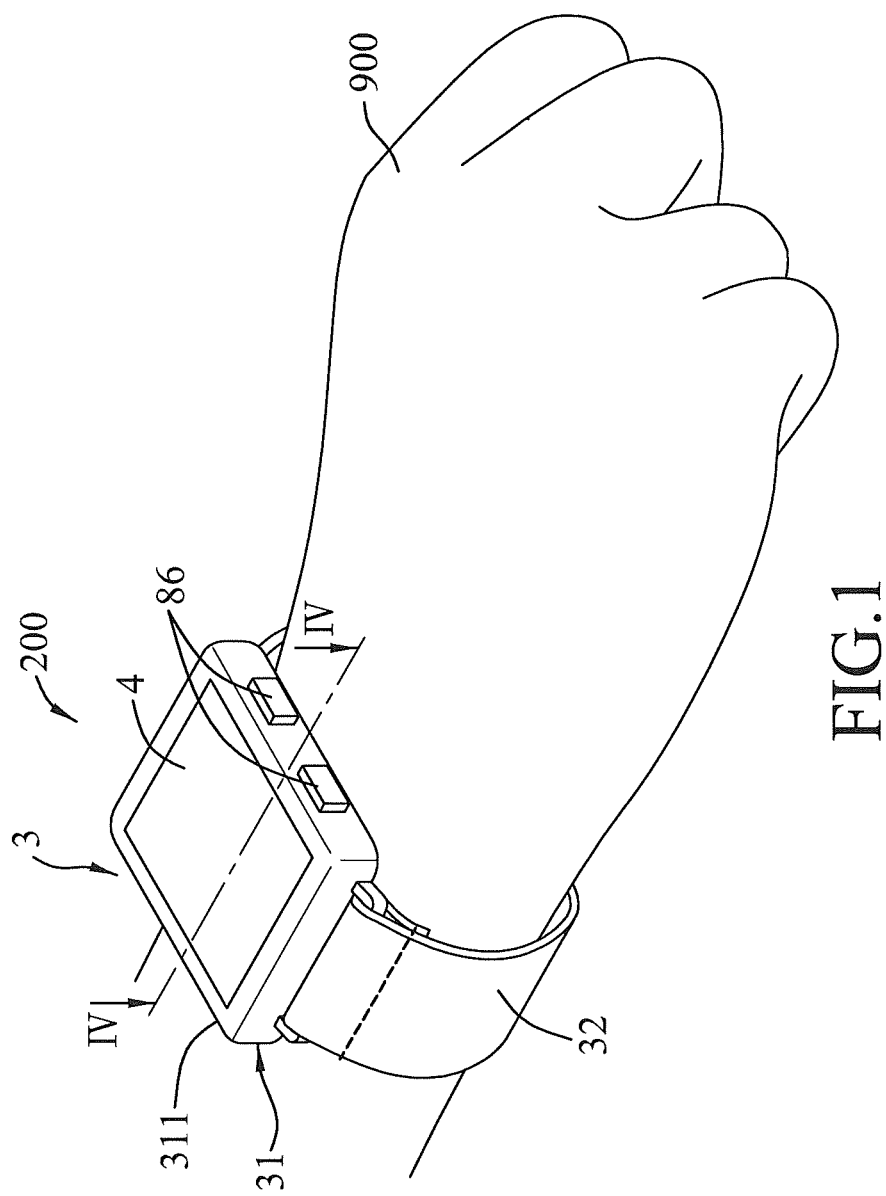
FIG. 1 is a perspective view illustrating a first embodiment of a device for performing angiography and phototherapy on a subject according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
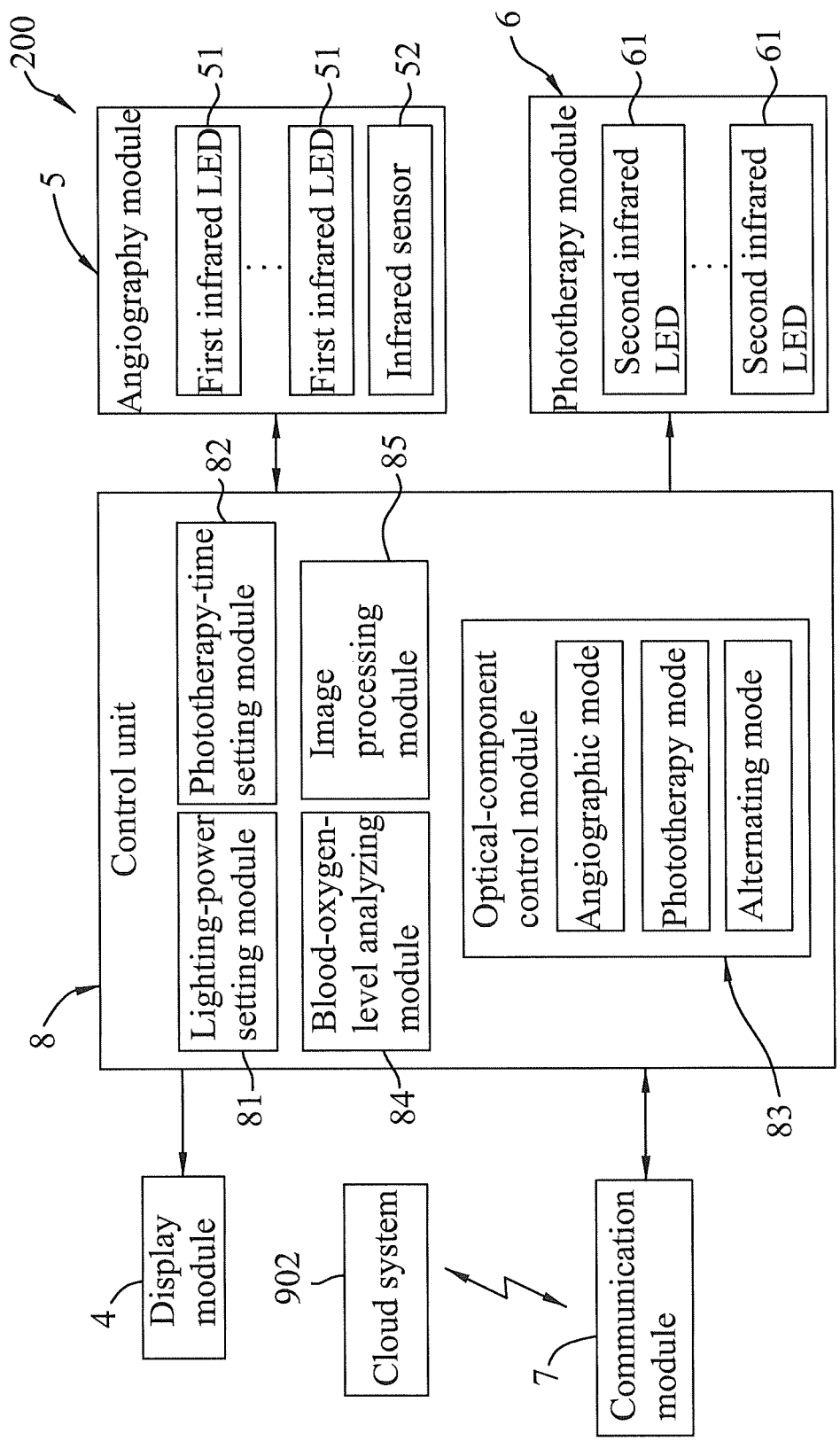
FIG. 2 is a block diagram illustrating the first embodiment of the device according to the disclosure.

Referring to FIGS. 1 and 2, a first embodiment of a device 200 for performing angiography and phototherapy on an arteriovenous (AV) fistula (or an AV graft) 901 (see FIGS. 3 and 4) of a limb 900 of a subject is illustrated. In this embodiment, the subject is a patient who is treated with hemodialysis.

The device 200 includes a carrier 3, a display module 4, an angiography module 5, a phototherapy module 6, a communication module 7 and a control unit 8.

The display module 4, the angiography module 5, the phototherapy module 6, the communication module 7 and the control unit 8 are all disposed on the carrier 3, and each of the display module 4, the angiography module 5, the phototherapy module 6 and the communication module 7 is coupled to the control unit 8 to communicate therewith. The device 200 is capable of communicating and performing data transmission with a cloud system 902 (e.g., a cloud server) via the communication module 7.

Figure 3:
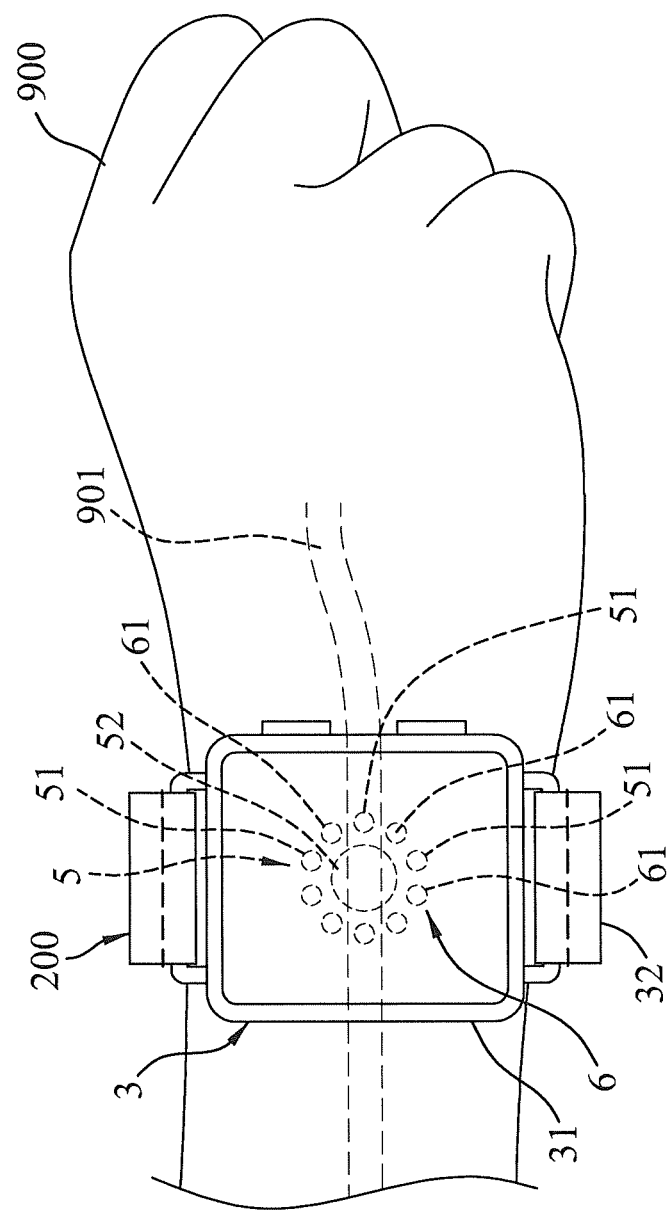
FIG. 3 is a schematic diagram illustrating a top view of the first embodiment of the device disposed on the subject according to the disclosure.
Figure 4:
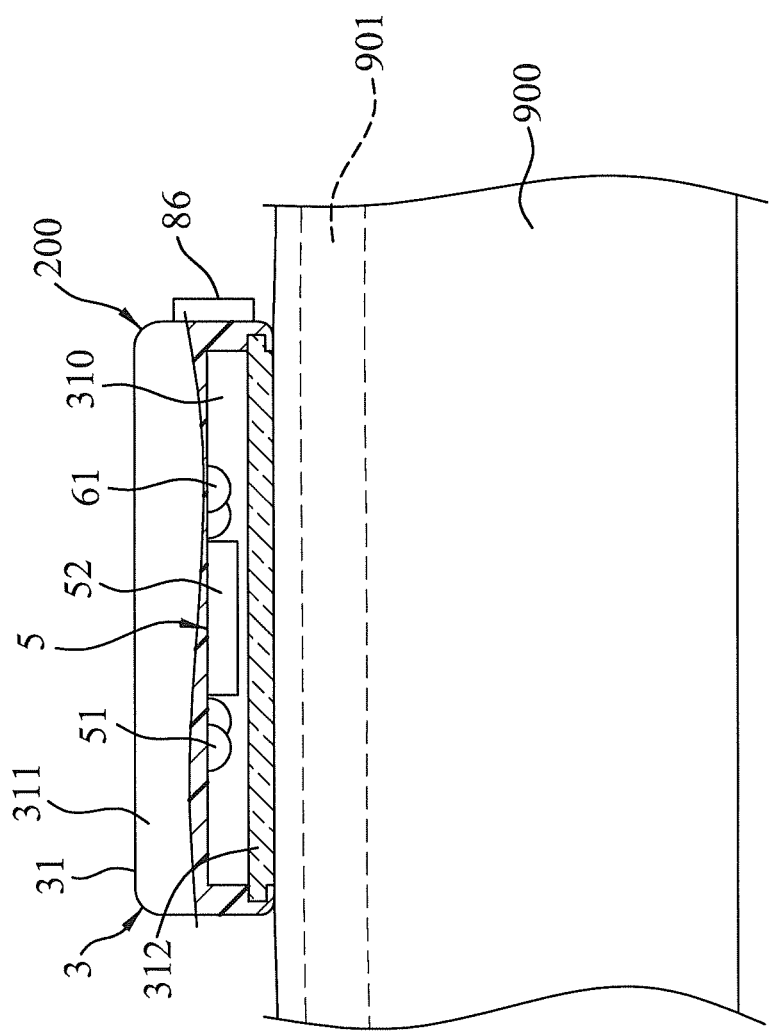
FIG. 4 is a schematic diagram illustrating a partly sectional view taken along an imaginary sectional line (IV-IV) in FIG. 1.

Referring to FIGS. 1, 3 and 4, the carrier 3 is configured to be disposed on the limb 900 of the subject, and includes a housing 31 and a binding component 32. The housing 31 is configured to abut against the limb 900, and defines an accommodating space 310 having an opening to face the limb 900. Specifically, the housing 31 includes a housing body 311 defining the accommodating space 310, and an optical filter 312 mounted to the housing body 311 and closing the opening of the accommodating space 310. The optical filter 312 may be implemented as a colored glass plate or plastic device, and is used to filter out ambient light having wavelengths that may affect operation of the device 200 (e.g., beyond a range of wavelengths of light emitted by the angiography module 5 and the phototherapy module 6) and being considered as noise. As shown in FIGS. 1 and 3, the binding component 32 is a strap attached to the housing 31, and is configured to tie the housing 31 to the limb 900 of the subject in a manner that the housing 31 is positioned over at least a part of the AV fistula (or the AV graft) 901 of the subject and that the optical filter 312 of the housing 31 abuts against the limb 900. It should be noted that the type of the binding component 32 is not limited to the disclosure herein and may vary in other embodiments.

The display module 4 is mounted on the housing body 311 and is exposed from a top of the housing body 311 opposite to the optical filter 312. In this embodiment, the display module 4 may be a liquid-crystal display (LCD), a light-emitting diode (LED) display, a plasma display panel, a projection display or the like. However, implementation of the display module 4 is not limited to the disclosure herein and may vary in other embodiments.

Figure 5:
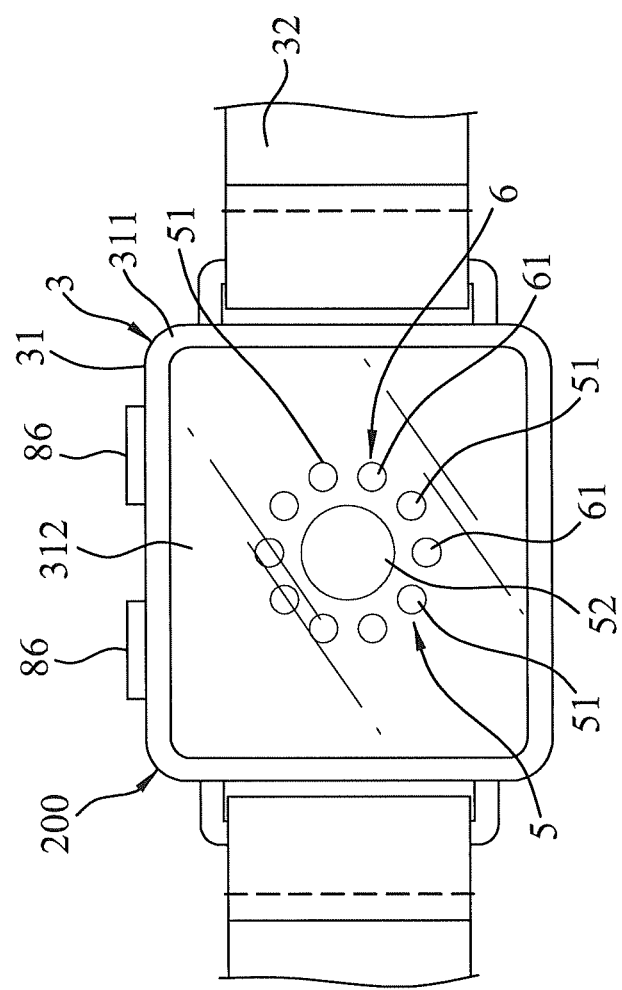
FIG. 5 is a schematic diagram illustrating a bottom view of the first embodiment of the device according to the disclosure.

Referring to FIGS. 3, 4 and 5, the angiography module 5 is disposed in the accommodating space 310 of the housing body 311 and is mounted on the housing body 311. The angiography module 5 includes a plurality of first infrared light-emitting diodes (LEDs) 51 and an infrared sensor 52 that are exposed in the accommodating space 310. The first infrared LEDs 51 are arranged around the infrared sensor 52, and are configured to emit first infrared light through the optical filter 312 to irradiate the limb 900. In this embodiment, the first infrared LEDs 51 are configured to emit the first infrared light having a wavelength of about 1.3 micrometers. The first infrared light emitted toward the limb 900 penetrates the skin of the limb 900 and then is absorbed and reflected by the AV fistula (or the AV graft) 901 and surrounding tissues of the AV fistula (or the AV graft) 901. The infrared sensor 52 is configured to sense a part of the first infrared light reflected off the limb 900 (i.e., reflected by the AV fistula (or the AV graft) 901 and the surrounding tissues) to generate a result of sensing. It is worth to note that a degree of absorption of the first infrared light by the AV fistula (or the AV graft) 901 is different from a degree of absorption of the first infrared light by the surrounding tissues of the AV fistula (or the AV graft) 901 and such difference is significant, and thus the result of sensing that contains information related to such difference can be utilized to perform further analysis and to generate an image of the AV fistula (or the AV graft) 901, e.g., an angiogram of the AV fistula (or the AV graft) 901.

The phototherapy module 6 is disposed in the accommodating space 310 of the housing body 311 and is mounted on the housing body 311. The phototherapy module 6 includes a plurality of second infrared LEDs 61 that are exposed in the accommodating space 310 and that are arranged around the infrared sensor 52. The second infrared LEDs 61 are configured to emit second infrared light through the optical filter 312 to irradiate the limb 900 for phototherapy. In this embodiment, the second infrared LEDs 61 are configured to emit the second infrared light having a wavelength ranging from one to twenty micrometers. In this way, the AV fistula (or the AV graft) 901 and surrounding tissues of the AV fistula (or the AV graft) 901 are irradiated by the second infrared light penetrating the skin of the limb 900.

In this embodiment, the first infrared LEDs 51 and the second infrared LEDs 61 are alternately arranged in a circle to surround the infrared sensor 52. That is to say, each of the first infrared LEDs 51 is disposed between two of the second infrared LEDs 61, and each of the second infrared LEDs 61 is disposed between two of the first infrared LEDs 51.

The control unit 8 (see FIG. 2) may be implemented by a system on a chip (SoC), or any circuit configurable/programmable in a software manner and/or hardware manner to implement functionalities discussed in this disclosure. Referring to FIGS. 1 and 2, the control unit 8 includes a lighting-power setting module 81, a phototherapy-time setting module 82, an optical-component control module 83, a blood-oxygen-level analyzing module 84, an image processing module 85 and a plurality of control buttons 86.

It should be noted that each of the lighting-power setting module 81, the phototherapy-time setting module 82, the optical-component control module 83, the blood-oxygen-level analyzing module 84 and the image processing module 85 may be implemented by one of hardware, firmware, software, and any combination thereof. For example, the lighting-power setting module 81, the phototherapy-time setting module 82, the optical-component control module 83, the blood-oxygen-level analyzing module 84 and the image processing module 85 may be implemented to be software modules in a program, where the software modules contain codes and instructions to carry out specific functionalities, and can be called individually or together to fulfill functionalities of the control unit 8 of this disclosure. The above-mentioned modules may be embodied in: executable software as a set of logic instructions stored in a machine- or computer-readable storage medium of a memory such as random access memory (RAM), read only memory (ROM), programmable ROM (PROM), firmware, flash memory, etc.; configurable logic such as programmable logic arrays (PLAs), field programmable gate arrays (FPGAs), complex programmable logic devices (CPLDs), etc.; fixed-functionality logic hardware using circuit technology such as application specific integrated circuit (ASIC), complementary metal oxide semiconductor (CMOS), transistor-transistor logic (TTL) technology, etc.; or any combination thereof.

The control buttons 86 are embedded in an external surface of the housing body 311, and are operable for controlling the lighting-power setting module 81, the phototherapy-time setting module 82, the optical-component control module 83, the blood-oxygen-level analyzing module 84 and the image processing module 85.

The optical-component control module 83 is configured to control operation of the angiography module 5 and the phototherapy module 6. Specifically, the optical-component control module 83 is configured to operate in an angiographic mode for performing blood-oxygen-level analysis and angiographic sensing. The angiographic mode has a first stage, and a second stage following the first stage.

In the first stage of the angiographic mode, the optical-component control module 83 is configured to control the first infrared LEDs 51 to repeatedly (periodically) emit the first infrared light with a preset frequency (e.g., 8000 times per second), and to simultaneously control the infrared sensor 52 to sense a part of the first infrared light reflected off the limb 900 to generate a result of sensing every time the first infrared LEDs 51 are controlled to emit the first infrared light, so as to generate a plurality of results of sensing corresponding respectively to plural times of emission of the first infrared light. The blood-oxygen-level analyzing module 84 is configured to determine a periodic variation of blood oxygen level (which contains information of a period of the variation of blood oxygen level) by analyzing the results of sensing generated in the first stage. Since implementation of blood-oxygen-level analysis by using infrared light has been well known to one skilled in the relevant art, detailed explanation of the same is omitted herein for the sake of brevity.

In the second stage of the angiographic mode, the optical-component control module 83 is configured to estimate, based on the periodic variation of blood oxygen level thus determined, at least one incoming peak time point at which a blood oxygen level reaches the maximum and at least one incoming nadir time point at which the blood oxygen level reaches the minimum. Next, at each of the incoming peak time point(s) and the incoming nadir time point(s) thus estimated, the optical-component control module 83 is configured to control the first infrared LEDs 51 to emit the first infrared light, and simultaneously control the infrared sensor 52 to sense a part of the first infrared light reflected off the limb 900 to generate a result of sensing. Specifically, in the second stage, the infrared sensor 52 will generate a plurality of results of sensing corresponding respectively to the incoming peak time point (s) and the incoming nadir time point (s).

The image processing module 85 is configured to generate an angiogram based on the result of sensing generated by the infrared sensor 52 of the angiography module 5. Specifically, the image processing module 85 is configured to analyze the result of sensing generated at the incoming peak time point to generate an angiogram, and to analyze the result of sensing generated at the incoming nadir time point to generate another angiogram. The angiogram generated at the incoming peak time point corresponds to maximal dilation of the AV fistula (or the AV graft) 901, and the angiogram generated at the incoming nadir time point corresponds to maximal contraction of the AV fistula (or the AV graft) 901. Since implementation of generating the angiogram has been well known to one skilled in the relevant art, detailed explanation of the same is omitted herein for the sake of brevity.

After the angiograms are generated, the display module 4 is configured to display each of the angiograms. In some embodiments, the communication module 7 is configured to transmit the angiograms by using techniques of one of wired communication and wireless communication. The communication module 7 may be implemented to be a network interface controller or a wireless transceiver that supports wired communication standards and/or wireless communication standards, such as Bluetooth technology standards, Wi-Fi wireless network protocols, the fourth generation technology standard for broadband cellular networks (4G) and the fifth generation technology standard for broadband cellular networks (5G). However, implementation of the communication module 7 is not limited to the disclosure herein and may vary in other embodiments.

The optical-component control module 83 is further configured to operate in a phototherapy mode to perform phototherapy by controlling the second infrared LEDs 61 to emit the second infrared light for a predetermined time one by one. The lighting-power setting module 81 is operable to set a lighting power by a user (e.g., the wearer of the device 200) operating the control buttons 86, and the optical-component control module 83 is configured to activate the second infrared LEDs 61 to emit the second infrared light with the lighting power thus set. Additionally, the phototherapy-time setting module 82 is operable to set a phototherapy time by the user operating the control buttons 86, and the optical-component control module 83 is configured to, in the phototherapy mode, time the phototherapy and terminate the phototherapy once the phototherapy time thus set is reached, and to cyclically activate the second infrared LEDs 61 to emit the second infrared light during the phototherapy time thus set. That is to say, the phototherapy mode will last for the phototherapy time thus set, and the optical-component control module 83 will, in the phototherapy mode, activate only one of the second infrared LEDs 61 to emit the second infrared light with the lighting power for the predetermined time (e.g., 5 seconds) that is shorter than the phototherapy time at a time, and then after the predetermined time has elapsed, deactivate said one of the second infrared LEDs 61 and activate another one of the second infrared LEDs 61 that is next to said one of the second infrared LEDs 61 in position to emit the second infrared light with the lighting power for the predetermined time, so on and so forth, up until the phototherapy mode ends (the phototherapy time has elapsed). In this way, the AV fistula (or the AV graft) 901 may be restored by irradiating different portions thereof with the second infrared light emitted by the second infrared LEDs 61.

The optical-component control module 83 is further configured to operate in an alternating mode to perform the first stage of the angiographic mode (once) at first, and then alternately perform the second stage of the angiographic mode and the phototherapy mode for a predetermined number of times (e.g., 4 times). In one embodiment, the second stage of the angiographic mode and the phototherapy mode are alternately performed until the phototherapy time elapsed.

For example, in a scenario where the phototherapy time is four hours (which is approximately a total duration of a hemodialysis treatment), the optical-component control module 83 performs the phototherapy mode for the first 40 minutes of each hour followed by the angiographic mode (which takes only a brief moment), and then stops for the last 20 minutes of said each hour.

A scenario of using the device 200 according to the disclosure is described in the following paragraphs for explanation. To attach the device 200 to the limb 900 of the subject, firstly, the optical filter 312 of the housing 31 abuts against a portion of the limb 900 over a part of the AV fistula (or the AV graft) 901 that is to be assessed and treated, e.g., a part that has been punctured a lot of times by needles in hemodialysis treatments, and then the housing 31 is tied to the limb 900 of the subject by the binding component 32 such that the first infrared LEDs 51 and the second infrared LEDs 61 are positioned over said part of the AV fistula (or the AV graft) 901 of the subject. Accordingly, the first infrared LEDs 51 and the second infrared LEDs 61 will surround the portion of limb 900 over the part of the AV fistula (or the AV graft) 901 that is to be assessed and treated. Following that, the optical-component control module 83 can be operated by the user operating the control buttons 86 to switch to one of the angiographic mode, the phototherapy mode and the alternating mode.

When operating in the angiographic mode, the optical-component control module 83 activates the blood-oxygen-level analyzing module 84 and the image processing module 85, and controls the angiography module 5 to sequentially perform the first and second stages of the angiographic mode for blood-oxygen-level analysis and angiographic sensing. Eventually, the angiograms of the AV fistula (or the AV graft) 901 in maximal dilation and maximal contraction are generated, and can be displayed on the display module 4. Further, to allow medical professionals to view the angiograms, the user can operate the control buttons 86 to switch between the angiograms shown on the display module 4. Furthermore, when the communication module 7 is coupled to the cloud system 902, the angiograms can be transmitted via the communication module 7 to the cloud system 902 so as to enable the cloud system 902 to analyze the angiograms by using techniques of big data analysis and to determine a damage condition of the AV fistula (or the AV graft) 901.

When operating in the phototherapy mode, the optical-component control module 83 activates the lighting-power setting module 81 and the phototherapy-time setting module 82 to allow the user to set the lighting power and the phototherapy time, respectively. Further, the optical-component control module 83 cyclically controls the second infrared LEDs 61 of the phototherapy module 6 to emit the second infrared light with the lighting power thus set until the phototherapy time thus set has elapsed.

When operating in the alternating mode, the optical-component control module 83 activates the lighting-power setting module 81 and the phototherapy-time setting module 82 to allow the user to set the lighting power and the phototherapy time, and further activates the blood-oxygen-level analyzing module 84 and the image processing module 85. In the alternating mode, the optical-component control module 83 first performs the first stage of the angiographic mode to control operation of the angiography module 5 and the blood-oxygen-level analyzing module 84 for blood-oxygen-level analysis, and then alternately performs the second stage of the angiographic mode to control operation of the angiography module 5 for angiographic sensing and the phototherapy mode to control the phototherapy module 6 for performing phototherapy until the phototherapy time elapsed.

Figure 6:
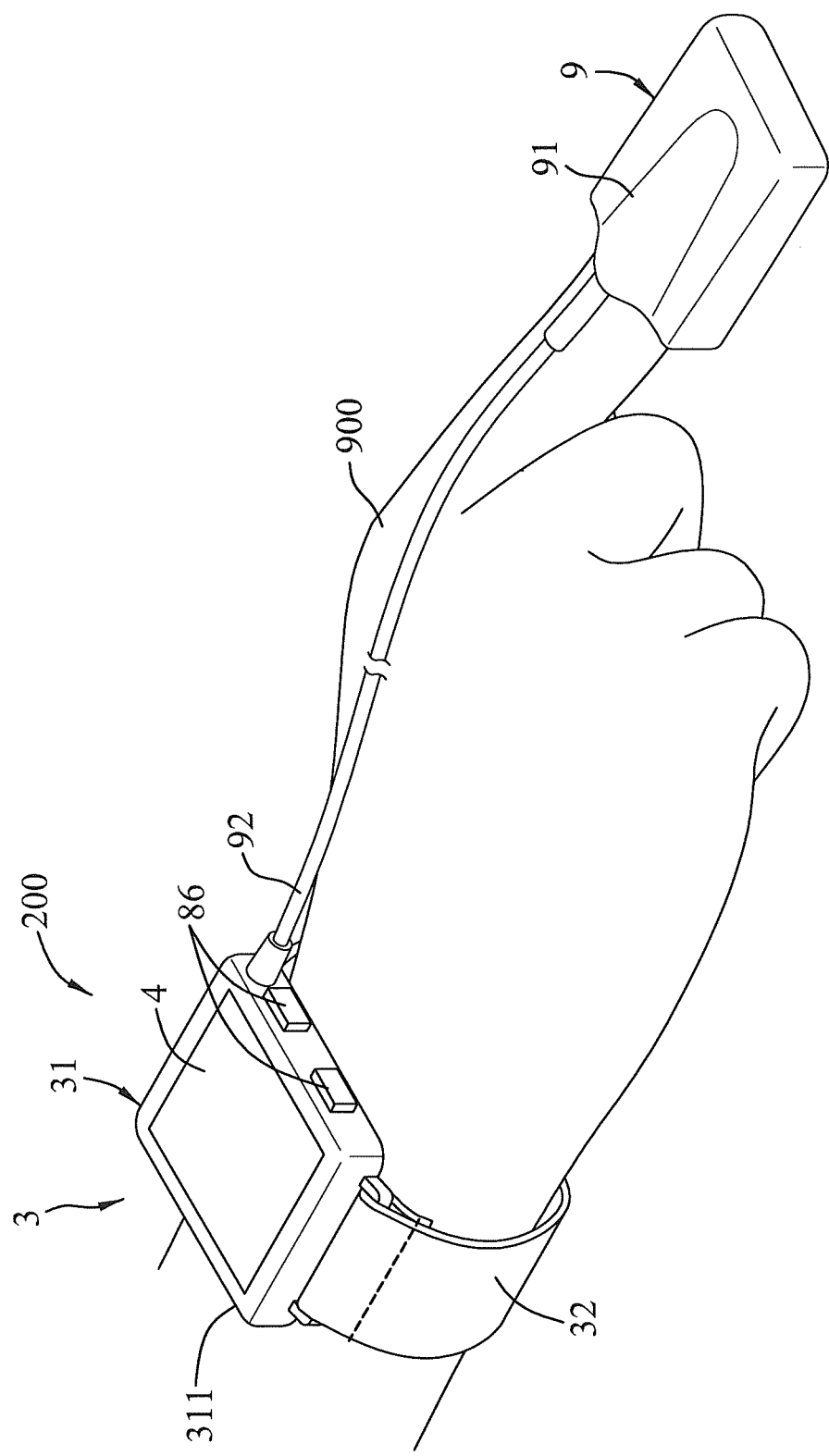
FIG. 6 is a perspective view illustrating a second embodiment of the device for performing angiography and phototherapy according to the disclosure.
Figure 7:
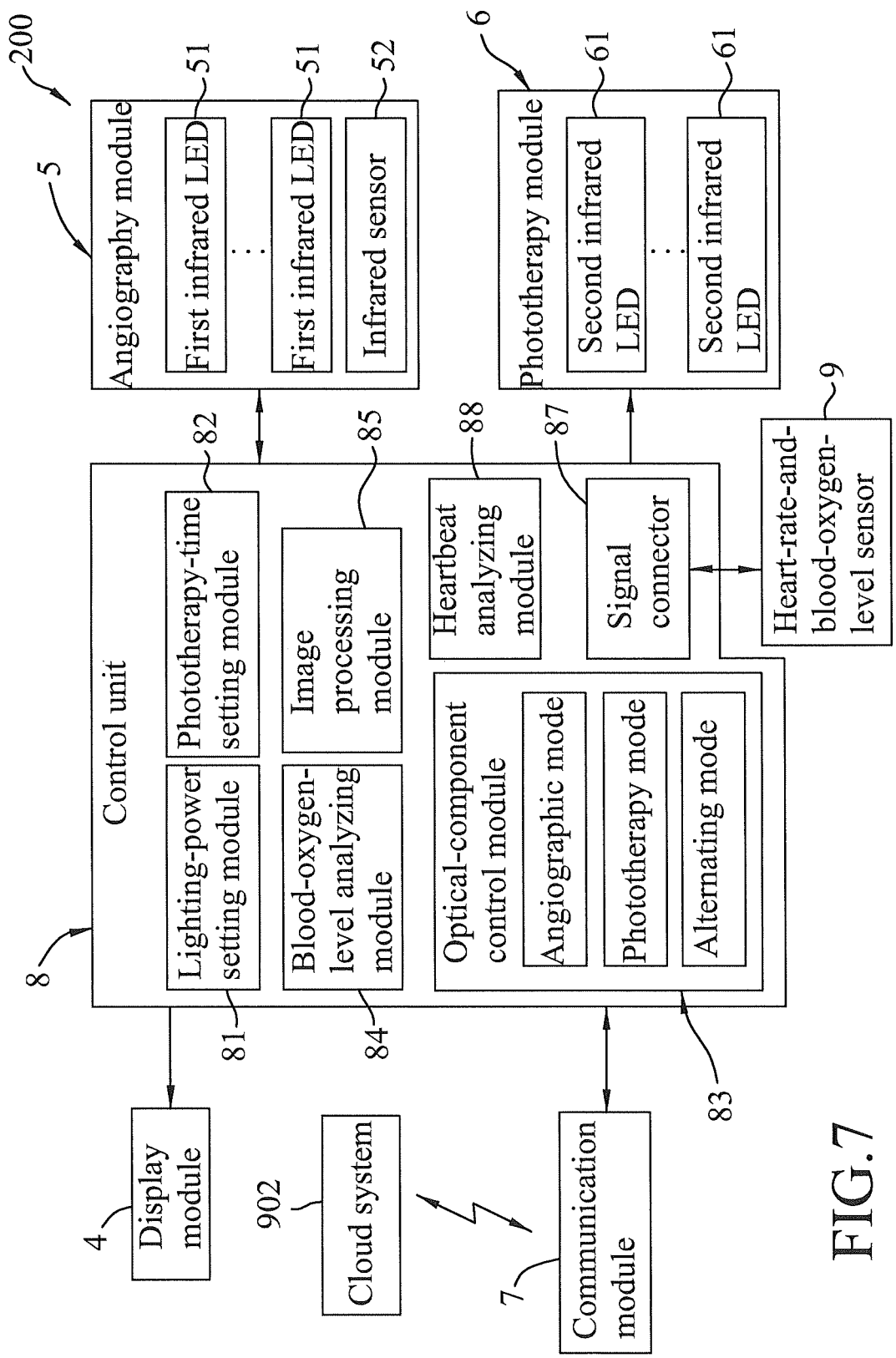
FIG. 7 is a block diagram illustrating the second embodiment of the device according to the disclosure.

Referring to FIGS. 6 and 7, a second embodiment of the device 200 for performing angiography and phototherapy is illustrated. The second embodiment is similar to the first embodiment of the device 200, and only differences between the first embodiment and the second embodiment will be described below for the sake of brevity.

In the second embodiment, the device 200 further includes a heart-rate-and-blood-oxygen-level (HRBOL) sensor 9 coupled to the control unit 8 to communicate therewith, and the control unit 8 further includes a signal connector 87 and a heartbeat analyzing module 88.

The signal connector 87 is exposed from the external surface of the housing body 311. The HRBOL sensor 9 is separably connected to the housing 31, and has a finger clip 91 and a signal wire 92. By inserting the signal wire 92 of the HRBOL sensor 9 to the signal connector 87 of the control unit 8, the HRBOL sensor 9 is coupled to the heartbeat analyzing module 88 of the control unit 8 via the signal connector 87 so as to communicate with the heartbeat analyzing module 88. It should be noted that the heartbeat analyzing module 88 may be implemented by one of hardware, firmware, software, and any combination thereof. For example, the heartbeat analyzing module 88 may be embodied in: executable software as a set of logic instructions stored in a machine- or computer-readable storage medium of a memory such as random access memory (RAM), read only memory (ROM), programmable ROM (PROM), firmware, flash memory, etc.; configurable logic such as programmable logic arrays (PLAs), field programmable gate arrays (FPGAs), complex programmable logic devices (CPLDs), etc.; fixed-functionality logic hardware using circuit technology such as application specific integrated circuit (ASIC), complementary metal oxide semiconductor (CMOS), transistor-transistor logic (TTL) technology, etc.; or any combination thereof.

The finger clip 91 of the HRBOL sensor 9 is to be worn on a finger of the subject. The HRBOL sensor 9 is configured to detect the heart rate and the blood oxygen level of the subject by using optical techniques so as to generate HRBOL data to include the heart rate and the blood oxygen level, and to transmit the HRBOL data thus generated to the heartbeat analyzing module 88 via the signal wire 92 of the HRBOL sensor 9. Since detection of the heart rate and the blood oxygen level by using optical techniques has been well known to one skilled in the relevant art, detailed explanation of the same is omitted herein for the sake of brevity.

The heartbeat analyzing module 88 is configured to receive the HRBOL data, and to determine a periodic variation of heartbeat that contains information of a cardiac cycle by analyzing information that is contained in the HRBOL data thus received and that is related to variation of the heart rate and variation of the blood oxygen level within a predefined time period. In one embodiment, the heartbeat analyzing module 88 is further configured to display waveforms respectively of the variation of the heart rate and the variation of the blood oxygen level at the same time on the display module 4 of the device 200.

The optical-component control module 83 is further configured to not activate the blood-oxygen-level analyzing module 84 of the control unit 8 when the heartbeat analyzing module 88 is coupled to the HRBOL sensor 9 and the optical-component control module 83 operates in the angiographic mode or in the alternating mode.

In particular, the optical-component control module 83 is configured to activate, when the optical-component control module 83 operates in the first stage of the angiographic mode, the heartbeat analyzing module 88 to determine the periodic variation of heartbeat by analyzing the HRBOL data. In the second stage of the angiographic mode, the optical-component control module 83 is configured to estimate, based on the periodic variation of heartbeat thus determined, an incoming systole time point which corresponds to systole of heart and an incoming diastole time point which corresponds to diastole of heart. Next, at each of the incoming systole time point and the incoming diastole time point thus estimated, the optical-component control module 83 is configured to control the first infrared LEDs 51 to emit the first infrared light multiple times, and simultaneously control the infrared sensor 52 to sense a part of the first infrared light reflected off the limb 900 each time the first infrared LEDs 51 emit the first infrared light, so as to generate multiple results of sensing corresponding to the incoming systole time point and multiple results of sensing corresponding to the incoming diastole time point. In one embodiment, the optical-component control module 83 is configured to estimate a plurality of incoming systole time points and a plurality of incoming diastole time points.

Thereafter, for each of the incoming systole time point(s), the image processing module 85 is configured to analyze each of the results of sensing generated at the incoming systole time point to generate an angiogram, and to perform feature extraction and image synthesis on the angiograms generated respectively from the results of sensing generated at the incoming systole time point, so as to generate a synthesized angiogram corresponding to the incoming systole time point. Similarly, for each of the incoming diastole time point(s), the image processing module 85 is configured to analyze each of the results of sensing generated at the incoming diastole time point to generate an angiogram, and to perform feature extraction and image synthesis on the angiograms generated respectively from the results of sensing generated at the incoming diastole time point, so as to generate another synthesized angiogram corresponding to the incoming diastole time point. Since implementation of feature extraction and image synthesis has been well known to one skilled in the relevant art, detailed explanation of the same is omitted herein for the sake of brevity.

In one embodiment, the image processing module 85 is configured to control, at each of the incoming systole time points and the incoming diastole time points thus estimated, the first infrared LEDs 51 to emit the first infrared light only once, and simultaneously control the infrared sensor 52 to sense a part of the first infrared light reflected off the limb 900 as the first infrared LEDs 51 emit the first infrared light, so as to generate a plurality of results of sensing corresponding respectively to the incoming systole time points and the incoming diastole time points (i.e., one result of sensing for one time point). Then, the image processing module 85 is configured to analyze the result of sensing generated at each of the incoming systole time points to generate an angiogram, and to perform feature extraction and image synthesis on the angiograms corresponding respectively to the incoming systole time points so as to generate a synthesized angiogram. Similarly, the image processing module 85 is configured to analyze the result of sensing generated at each of the incoming diastole time points to generate an angiogram, and to perform feature extraction and image synthesis on the angiograms corresponding respectively to the incoming diastole time points so as to generate another synthesized angiogram.

In summary, the device 200 according to the disclosure performs angiography by utilizing the angiography module 5 to generate a result of sensing based on infrared light reflected off an AV fistula (or an AV graft) 901 under limb skin of a subject, and utilizing the image processing module 85 to generate an angiogram based on the result of sensing. Moreover, the device 200 according to the disclosure performs phototherapy by utilizing the phototherapy module 6 to emit infrared light to irradiate the AV fistula (or the AV graft) of the subject. The angiogram thus generated can be displayed on the display module 4 of the device 200, and can be transmitted via the communication module 7 of the device 200 to a cloud system 902 for further analysis (e.g., by techniques of big data). Thus, medical professional(s) may be able to assess a damage condition of the AV fistula (or the AV graft), and thus to appropriately restore the AV fistula (or the AV graft) in time based on such assessment. In this way, a service life of the AV fistula (or the AV graft) may be extended.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A device for performing angiography and phototherapy on a subject, said device comprising:

a carrier configured to be disposed on a limb of the subject, and including
a housing that is configured to abut against the limb, that defines an accommodating space having an opening to face the limb, and that includes an optical filter closing said opening of said accommodating space;

an angiography module disposed in said accommodating space of said housing, and including
a plurality of first infrared light-emitting diodes (LEDs) that are configured to emit first infrared light through said optical filter to irradiate the limb, and
an infrared sensor that is configured to sense a part of the first infrared light reflected off the limb to generate a result of sensing;

a phototherapy module disposed in said accommodating space of said housing, and including
a plurality of second infrared LEDs that are configured to emit second infrared light through said optical filter to irradiate the limb for phototherapy; and a control unit coupled to said angiography module and said phototherapy module to communicate therewith, and including
an optical-component control module that is configured to control operation of said angiography module and said phototherapy module, and
an image processing module that is configured to generate an angiogram based on the result of sensing generated by said infrared sensor of said angiography module, wherein:
said optical-component control module is configured to operate in an angiographic mode having a first stage, and a second stage following the first stage;
in the first stage of the angiographic mode, said optical-component control module is configured to control said first infrared LEDs to repeatedly emit the first infrared light with a preset frequency, and to simultaneously control said infrared sensor to sense a part of the first infrared light reflected off the limb to generate a result of sensing every time said first infrared LEDs emit the first infrared light, so as to generate a plurality of results of sensing corresponding respectively to plural times of emission of the first infrared light;
said control unit further includes a blood-oxygen-level analyzing module that is configured to determine a periodic variation of blood oxygen level by analyzing the results of sensing generated in the first stage;
in the second stage of the angiographic mode, said optical-component control module is configured to:
estimate, based on the periodic variation of blood oxygen level thus determined, an incoming peak time point at which a blood oxygen level reaches the maximum and an incoming nadir time point at which the blood oxygen level reaches the minimum,
control, at each of the incoming peak time point and the incoming nadir time point thus estimated, said first infrared LEDs to emit the first infrared light, and
simultaneously control said infrared sensor to sense, for each of the incoming peak time point and the incoming nadir time point, a part of the first infrared light reflected off the limb, so as to generate a result of sensing corresponding to the incoming peak time point and a result of sensing corresponding to the incoming nadir time point;

said image processing module is configured to analyze the result of sensing generated at the incoming peak time point to generate an angiogram, and analyze the result of sensing generated at the incoming nadir time point to generate another angiogram; and said first infrared LEDs and said second infrared LEDs are alternately arranged in a circle to surround said infrared sensor.

2. The device as claimed in claim 1, wherein said optical-component control module is further configured to operate in a phototherapy mode to perform phototherapy by controlling said second infrared LEDs to emit the second infrared light for a predetermined time one by one.

3. The device as claimed in claim 2, wherein said control unit further includes a lighting-power setting module that is operable to set a lighting power, and said optical-component control module is configured to activate said second infrared LEDs to emit the second infrared light with the lighting power thus set.

4. The device as claimed in claim 2, wherein:

said control unit further includes a phototherapy-time setting module that is operable to set a phototherapy time; and said optical-component control module is configured to, in the phototherapy mode, cyclically activate said second infrared LEDs to emit the second infrared light during the phototherapy time thus set.

5. The device as claimed in claim 1, wherein said optical-component control module is further configured to operate in an alternating mode to perform the first stage of the angiographic mode at first, and then alternately perform the second stage of the angiographic mode and the phototherapy mode for a predetermined number of times.

6. The device as claimed in claim 1, further comprising a display module disposed on said carrier, coupled to said control unit to communicate therewith, and configured to display the angiogram.

7. The device as claimed in claim 1, further comprising a display module disposed on said carrier, coupled to said control unit to communicate therewith, and configured to display the angiogram.

8. The device as claimed in claim 1, further comprising a communication module disposed on said carrier, coupled to said control module to communicate therewith, and configured to transmit the angiogram by using techniques of one of wired communication and wireless communication.

9. The device as claimed in claim 1, wherein each of said first infrared LEDs is configured to emit the first infrared light having a wavelength of 1.3 micrometers, and each of said second infrared LEDs is configured to emit the second infrared light having a wavelength ranging from one to twenty micrometers.

10. The device as claimed in claim 1, wherein said optical-component control module is further configured to operate in a phototherapy mode to perform phototherapy by controlling said second infrared LEDs to emit the second infrared light for a predetermined time one by one.

11. The device as claimed in claim 10, wherein said control unit further includes a lighting-power setting module that is operable to set a lighting power, and said optical-component control module is configured to activate said second infrared LEDs to emit the second infrared light with the lighting power thus set.

12. The device as claimed in claim 10, wherein:

said control unit further includes a phototherapy-time setting module that is operable to set a phototherapy time; and said optical-component control module is configured to, in the phototherapy mode, cyclically activate said second infrared LEDs to emit the second infrared light during the phototherapy time thus set.

* * * * *